(12) United States Patent
Kavusi

(10) Patent No.: US 10,702,142 B1
(45) Date of Patent: Jul. 7, 2020

(54) FUNCTIONAL RETINAL IMAGING WITH IMPROVED ACCURACY

(71) Applicant: Verily Life Sciences LLC, Mountain View, CA (US)

(72) Inventor: Sam Kavusi, Menlo Park, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 120 days.

(21) Appl. No.: 15/971,669

(22) Filed: May 4, 2018

Related U.S. Application Data

(60) Provisional application No. 62/508,784, filed on May 19, 2017.

(51) Int. Cl.
| | |
|---|---|
| *A61B 3/02* | (2006.01) |
| *A61B 3/024* | (2006.01) |
| *G06T 7/00* | (2017.01) |
| *G06T 3/40* | (2006.01) |
| *A61B 3/113* | (2006.01) |

(Continued)

(52) U.S. Cl.
CPC ............ *A61B 3/024* (2013.01); *A61B 3/0025* (2013.01); *A61B 3/0033* (2013.01); *A61B 3/0041* (2013.01); *A61B 3/0091* (2013.01); *A61B 3/113* (2013.01); *A61B 3/14* (2013.01); *G06T 3/4038* (2013.01); *G06T 7/0002* (2013.01); *G06T 2200/32* (2013.01); *G06T 2207/30041* (2013.01); *G06T 2207/30168* (2013.01)

(58) Field of Classification Search
CPC ..... A61B 3/102; A61B 3/0025; A61B 3/1015; A61B 3/14; A61B 3/113; A61B 3/152; A61B 3/112; A61B 3/1035; A61B 3/117; A61B 3/132; A61B 3/107; A61B 3/103; A61B 3/024; A61B 3/12; A61B 3/1005; A61B 3/0091; A61B 3/1025; A61B 3/0008; A61B 3/0041; A61B 3/0083; A61B 3/063; A61B 1/00172
USPC ........ 351/200, 205–206, 209–211, 221, 222, 351/243–246
See application file for complete search history.

(56) References Cited

U.S. PATENT DOCUMENTS

| | | |
|---|---|---|
| 6,733,129 B2 | 5/2004 | Masaki |
| 7,458,685 B2 | 12/2008 | Liang et al. |
| 7,499,634 B2 | 3/2009 | Yogesan et al. |

(Continued)

OTHER PUBLICATIONS

Bengtsson, B., et al., "A New Generation of Algorithms for Computerized Threshold Perimetry, SITA," ACTA Ophthalmologica Scandinavica 75(4):368-375, Aug. 1997.

(Continued)

*Primary Examiner* — Brandi N Thomas
(74) *Attorney, Agent, or Firm* — Christensen O'Connor Johnson Kindness PLLC

(57) ABSTRACT

A technique for performing a visual field test on an eye includes sequentially presenting visual stimuli to the eye on a display. A gaze direction of the eye is monitored with a camera to identify when the gaze direction has drifted from a fixation target. A first intended position associated with a first visual stimulus of the visual stimuli is offset to compensate for drifting of the gaze direction from the fixation target when the gaze direction is determined to have drifted during presentation of the first visual stimulus. User inputs indicating whether the user acknowledges observance of each of the visual stimuli presented are registered.

18 Claims, 8 Drawing Sheets

(51) Int. Cl.
*A61B 3/00* (2006.01)
*A61B 3/14* (2006.01)

(56) References Cited

U.S. PATENT DOCUMENTS

| | | | |
|---|---|---|---|
| 7,878,653 | B2 | 2/2011 | Ichikawa et al. |
| 7,954,949 | B2 | 6/2011 | Suzuki |
| 8,684,529 | B2 | 4/2014 | Johansson et al. |
| 8,811,657 | B2 | 8/2014 | Teiwes et al. |
| 8,955,971 | B2 | 2/2015 | Ichikawa et al. |
| 8,956,396 | B1* | 2/2015 | Friend ............... A61N 5/0622 607/88 |
| 9,125,559 | B2 | 9/2015 | Kersting et al. |
| 9,271,646 | B2 | 3/2016 | Neal et al. |
| 2013/0010259 | A1 | 1/2013 | Carnevale |
| 2013/0194548 | A1 | 8/2013 | Francis et al. |
| 2013/0208241 | A1* | 8/2013 | Lawson ............... A61B 3/0091 351/206 |
| 2013/0208243 | A1 | 8/2013 | Sakagawa |
| 2013/0329189 | A1 | 12/2013 | Mizucchi |
| 2014/0240666 | A1 | 8/2014 | Ootsuki |
| 2016/0174838 | A1 | 6/2016 | Herranen et al. |
| 2016/0262608 | A1* | 9/2016 | Krueger ............... A61B 3/0041 |
| 2016/0302665 | A1 | 10/2016 | Swedish et al. |
| 2016/0338589 | A1 | 11/2016 | Carrasco-Zevallos et al. |
| 2017/0325675 | A1* | 11/2017 | Liu ..................... A61B 3/0041 |

OTHER PUBLICATIONS

Centervue Website, Jan. 15, 2016, <http://www.centervue.com/> [retrieved Aug. 31, 2016], 5 pages.

de Matos, L., et al., "Coaxial Fundus Camera for Ophthalmology," Proceedings of SPIE Optical Engineering + Applications, vol. 9578, Current Developments in Lens Design and Optical Engineering XVI, San Diego, Aug. 9-13, 2015, pp. 957813-1-957813-5.

De Moraes, C.G., et al., "Management of Advanced Glaucoma: Characterization and Monitoring," Survey of Ophthalmology 61(5):597-615, Sep.-Oct. 2016.

DeHoog, E., and J. Schwiegerling, "Optimal Parameters for Retinal Illumination and Imaging in Fundus Cameras," Applied Optics 47(36):6769-6777, Dec. 2008.

Fan, X., and G. Yao, "Modeling Transient Pupillary Light Reflex Induced by a Short Light Flash," IEEE Transactions on Biomedical Engineering 58(1):36-42, Jan. 2011.

"Fundus Automated Perimetry," Compass, © 2017 Centervue SpA, <https://www.centervue.com/products/compass/> [retrieved Feb. 27, 2017], 16 pages.

Hastings, A., Jr., "Eye Box Performance Parameters for Non Pupil Forming Head/Helmet Mounted Displays," Dec. 6, 2006, paper submitted to University of Arizona, College of Optical Sciences (OPT 521), Phoenix, 6 pages.

"Standard Automated Perimetry," EyeWiki®, Jan. 8, 2017, <http://eyewiki.aao.org/Standard_Automated_Perimetry#Manual_vs._Automated_Perimetry> [retrieved Feb. 27, 2017], 7 pages.

Sugita, M., et al., "Motion Artifact and Speckle Noise Reduction in Polarization Sensitive Optical Coherence Tomography by Retinal Tracking," Biomedical Optics Express 5(1):106-122, Jan. 2014.

Swedish, T., et al., "eyeSelfie: Self Directed Eye Alignment Using Reciprocal Eye Box Imaging," Camera Culture MIT Media Lab, <http://web.media.mit.edu/~tswedish/projects/eyeSelfie.html> [retrieved Aug. 31, 2016], 3 pages; also published in ACM Transactions on Graphics 34(4):58, 2015, 3 pages.

Tran, K., et al., "Construction of an Inexpensive, Hand-Held Fundus Camera Through Modification of a Consumer 'Point-and-Shoot' Camera," Investigative Ophthalmology & Visual Science 53(12):7600-7607, Nov. 2012.

"TRC-NW8 Non-Mydriatic Retinal Camera," © 2016 Topcon Medical Systems, Inc., Oakland, N.J., <http://www.topconmedical.com/products/trcnw8.htm> [retrieved Aug. 31, 2016], 1 page.

* cited by examiner

VISUAL FUNCTION SENSITIVITY MAPS

NUMERICAL
MAP 205

HEAT
MAP 210

```
           0   8 | 5  15
       10  9  17 |15  9   7
   22 15  5   7 |10  8   8 21
   22 20 24  25 |26 24  23 10  0
   ─────────────┼─────────────
   22 24 28  27 |26 28  25 26 24
   22 26 28  26 |27 23  21 22
      24 24  27 |25 26  25
          20  22|22 20
```

US 10,702,142 B1

FUNCTIONAL RETINAL IMAGING WITH IMPROVED ACCURACY

CROSS-REFERENCE TO RELATED APPLICATIONS

This application claims the benefit of U.S. Provisional Application No. 62/508,784, filed May 19, 2017, which is hereby incorporated by reference in its entirety.

TECHNICAL FIELD

This disclosure relates generally to ophthalmology devices, and in particular but not exclusively, relates to visual field testing.

BACKGROUND INFORMATION

Visual field testing is an important tool in the field of ophthalmology. It is currently the only test approved by the Food and Drug Administration for Glaucoma monitoring. Conventional visual field testing can take 10-30 minutes vs. 10-30 seconds for optical coherence tomography (OCT) or fundus imaging. One major reason for this length is due to inaccuracies in the conventional testing techniques. The Humphrey Visual Field Analyzer is one such tool currently available for performing a visual field test.

Accurate visual field testing is essential for tracking the progression of many neurological diseases including Glaucoma. The test involves asking a patient to direct their gaze on a fixation target while presenting stimuli to different parts of the retina (i.e., different parts of their field of view) and recording acknowledgement responses of the patient in the form of seen/not seen as registered by pushing a button. Knowing the gaze direction of the patient is important in order to identify which portion of the retina is being stimulated by a particular visual stimulus. The Humphrey Visual Field Analyzer operates in this manner.

However, the visual field data is often unreliable, especially for the target population of elderly whose vision is more often affected by Glaucoma. This unreliability stems from the patient's gaze direction drifting away from the fixation target while the visual stimuli are presented. Current tests attempt to ameliorate this problem by performing a gross gaze tracking of the pupil and reject responses when it is determined the user's gaze has drifted off the fixation target. Unfortunately, conventional gaze tracking based upon the pupil is only accurate to within a few degrees, which is not sufficiently accurate to identify with high precision when the user's gaze has drifted away from the fixation target. Repeating a presentation sequence of visual stimuli can improve the accuracy of visual field testing, but does so at the expense of prolonging the test. However, prolonging the test by repeating presentation sequences also has its limits in practice, as the patient's eyes begin to fatigue and their ability to maintain fixation on a fixation target reduces, thereby degrading the test results and increasing the number of rejected responses.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Embodiments of a system, apparatus, and method of operation for performing functional retinal imaging with improved accuracy that facilitate a visual field test and obtain high quality retinal images are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 1A:
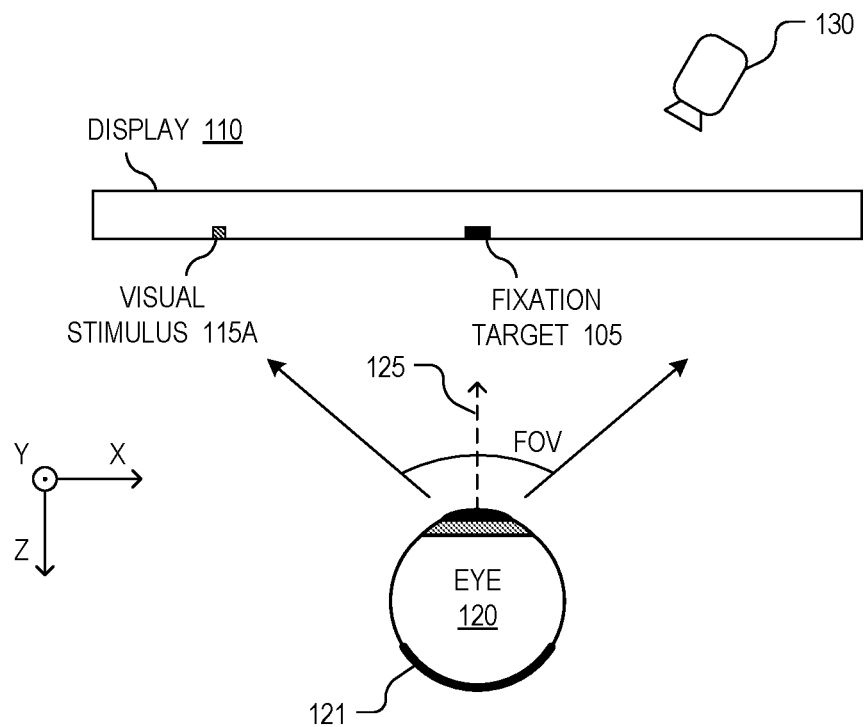
FIGS. 1A and 1B illustrate a fixation target and a display that sequentially presents visual stimuli to an eye during a visual field test, in accordance with an embodiment of the disclosure.
Figure 1B:
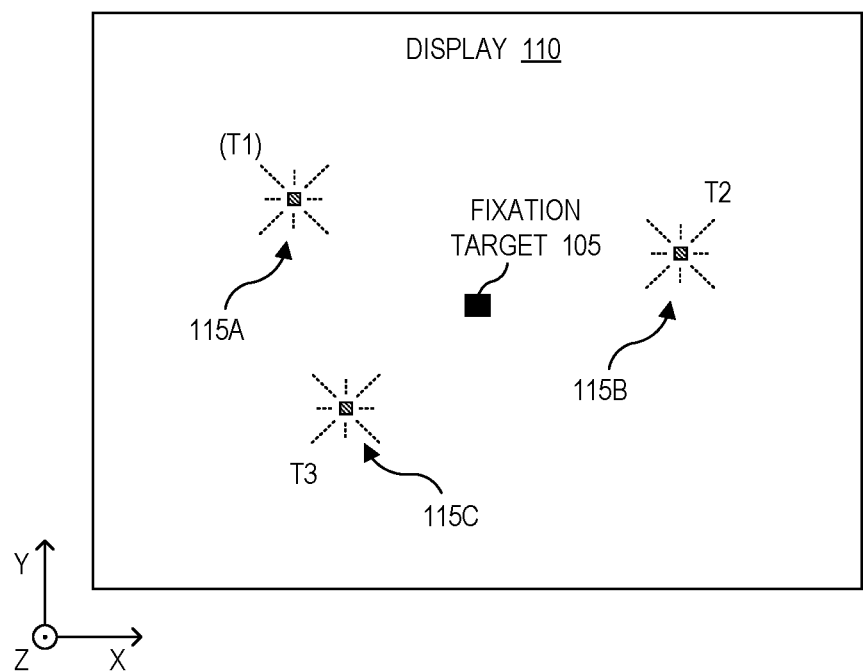

FIGS. 1A and 1B illustrate a fixation target 105 and a display 110 that sequentially presents visual stimuli 115A, B, and C (collectively 115) to an eye 120 at times T1, T2, and T3, respectively, during a visual field test, in accordance with an embodiment of the disclosure. The user is asked to direct their gaze direction 125 towards fixation target 105 and register acknowledgements of observing visual stimuli 115. Visual stimuli 115 are sequentially presented to the user throughout display 110 to measure a visual function sensitivity of eye 120 over the eye's field of view (FOV). The user inputs are collected and analyzed to generate a visual function sensitivity map.

Figure 2:
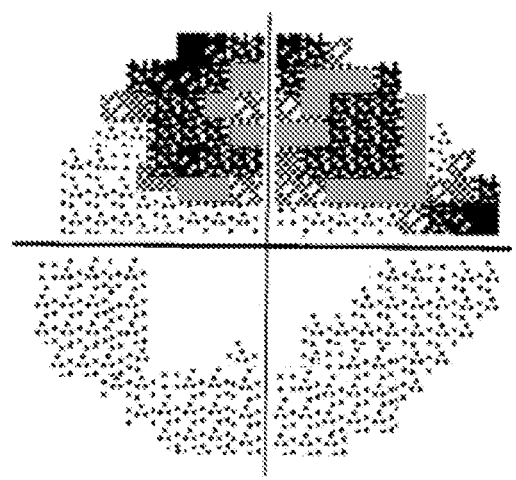
FIG. 2 illustrates two demonstrative types of visual function sensitivity maps, in accordance with an embodiment of the disclosure.

FIG. 2 illustrates two demonstrative types of visual function sensitivity maps, in accordance with an embodiment of the disclosure. The first visual function sensitivity map is a numerical map 205, which presents a grid of numbers that spatially indicate the sensitivity of the user's retina based upon the user's inputs or responses during the visual field testing. The numbers are indicative of the sensitivity of the retina at a given spatial location. The second visual function sensitivity map is a heat map 210, which presents similar data as numerical map 205, but graphically rather than numerically. Other forms of visual function sensitivity maps may be generated based upon the user inputs registered during the visual field testing.

Returning to FIGS. 1A and 1B, embodiments disclosed herein use camera 130 to monitor gaze direction 125 to identify when gaze direction 125 has drifted from fixation target 105. When gaze direction 125 is determined to have drifted during presentation of a given one of visual stimuli 115, an intended position associated with the given visual stimulus is offset so that the user inputs are registered and used. In other words, intended positions associated with visual stimuli are offset to compensate for a drifting gaze direction 125 instead of rejecting the user inputs. These offset intended positions can then be used when generating visual function sensitivity maps, thereby reducing the overall time of the visual field test. By reducing the overall length of the visual field test, eye 120 is less likely to fatigue, thereby reducing the likelihood gaze direction 125 will drift in the first place. In one embodiment, camera 130 is a retinal camera that tracks gaze direction in real-time by tracking anatomical features of retina 121.

Figure 3:
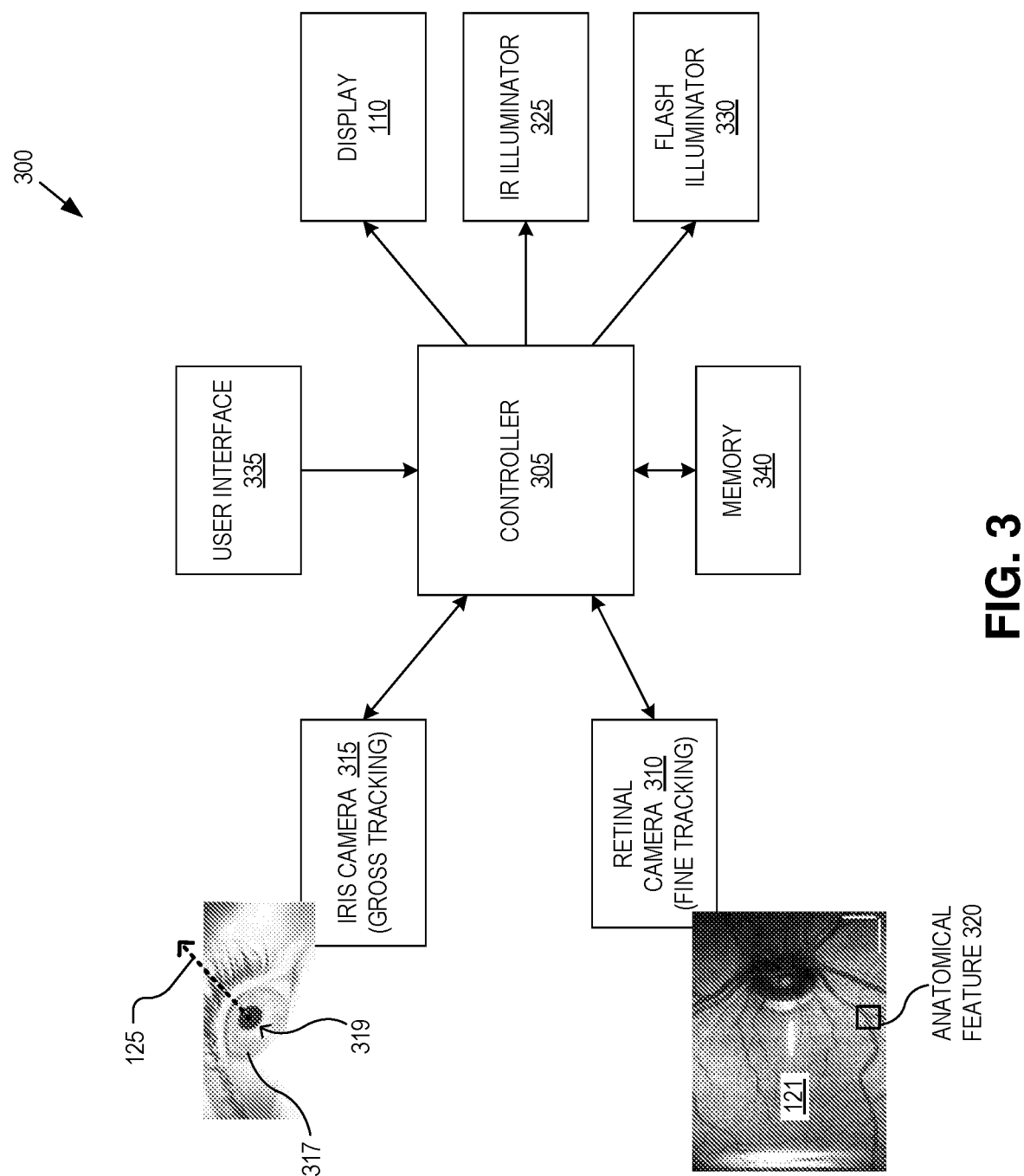
FIG. 3 is a functional block diagram illustrating components of an ophthalmic testing system for performing ophthalmic testing including visual field testing and retinal imaging, in accordance with an embodiment of the disclosure.

FIG. 3 is a functional block diagram illustrating components of an ophthalmic testing system 300 for performing ophthalmic testing including visual field testing and retinal imaging, in accordance with an embodiment of the disclosure. The illustrated embodiment of system 300 includes a controller 305, a retinal camera 310, an iris camera 315, a display 110, an infrared (IR) illuminator 325, a flash illuminator 330, and memory 340.

As mentioned above, display 110 operates as a visual field display to sequentially present visual stimuli 115 to eye 120. In one embodiment, display 110 is a micro-display (e.g., a liquid crystal display, organic light emitting diode display, a liquid crystal on silicon display, a light emitting diode array, etc.). In one embodiment, display 110 also presents fixation target 105 as a stationary element during visual field testing.

Iris camera 315 is included to provide gross gaze tracking and blink detection. For example, iris camera 315 may be focused on external portions of the eye, such as the iris 317 or pupil 319. In contrast, retinal camera 310 is configured to focus on retina 121 on the interior of eye 120 through pupil 319. Retinal camera 310 is operated to provide high-speed, high-precision gaze tracking (i.e., monitoring of gaze direction 125) by imaging and tracking anatomical features, such as feature 320, on retina 121. While conventional iris tracking cameras are capable of gaze tracking within tolerances measured in degrees (e.g., within 3 degrees), retinal tracking by retinal camera 310 is capable of gaze tracking within tolerances measured in millidegrees. These improved tolerances reduce image noise. In some embodiments, retinal camera 310 can also serve to produce high quality retinal or fundus images, in addition to, gaze tracking based on anatomical features.

IR illuminator 325 is provided to illuminate retina 121 and/or iris 317 with IR or far-IR illumination during gaze tracking. In one embodiment, IR illumination is output by IR illuminator 325 continuously during visual field examination to provide continuous real-time gross gaze direction monitoring and blink detection. Flash illuminator 330 provides visual spectrum, flash illumination when retinal camera 310 is acquiring retinal images. In one embodiment, the fine gaze detection performed by retinal camera 310 uses a series of high speed retinal images each acquired with flash illumination. In one embodiment, flash illuminator 330 outputs a white light flash. IR illuminator 325 and/or flash illuminator 330 may be implemented using one or more light emitting diodes (LEDs). In some embodiments, the functionalities of IR illuminator 325 and flash illuminator 330 may be integrated into a single illuminator.

User interface 335 provides a user feedback mechanism for registering user inputs indicating whether the user acknowledges observance of visual stimuli 115 presented on display 110. In one embodiment, user interface 335 may be a simple button or mechanical clicker. In other embodiments, user interface 335 may be a microphone for registering voice prompts. Other user interfaces may be implemented.

Controller 305 is coupled to the other components of system 300 to choreograph their operation for performing visual field tests and/or obtaining retinal or fundus images. Controller 305 may include a microprocessor for executing software/firmware instructions stored on memory 340. Controller 305 may include hardware logic (e.g., application specific integrated circuit, field programmable gate array, logic gates, etc.) for implementing the functionality described herein. In some embodiments, controller 305 acquires retinal images of retina 121 from retinal camera 310 and transfers those retinal images into memory 340 for storage and/or subsequent image processing.

Figure 4:
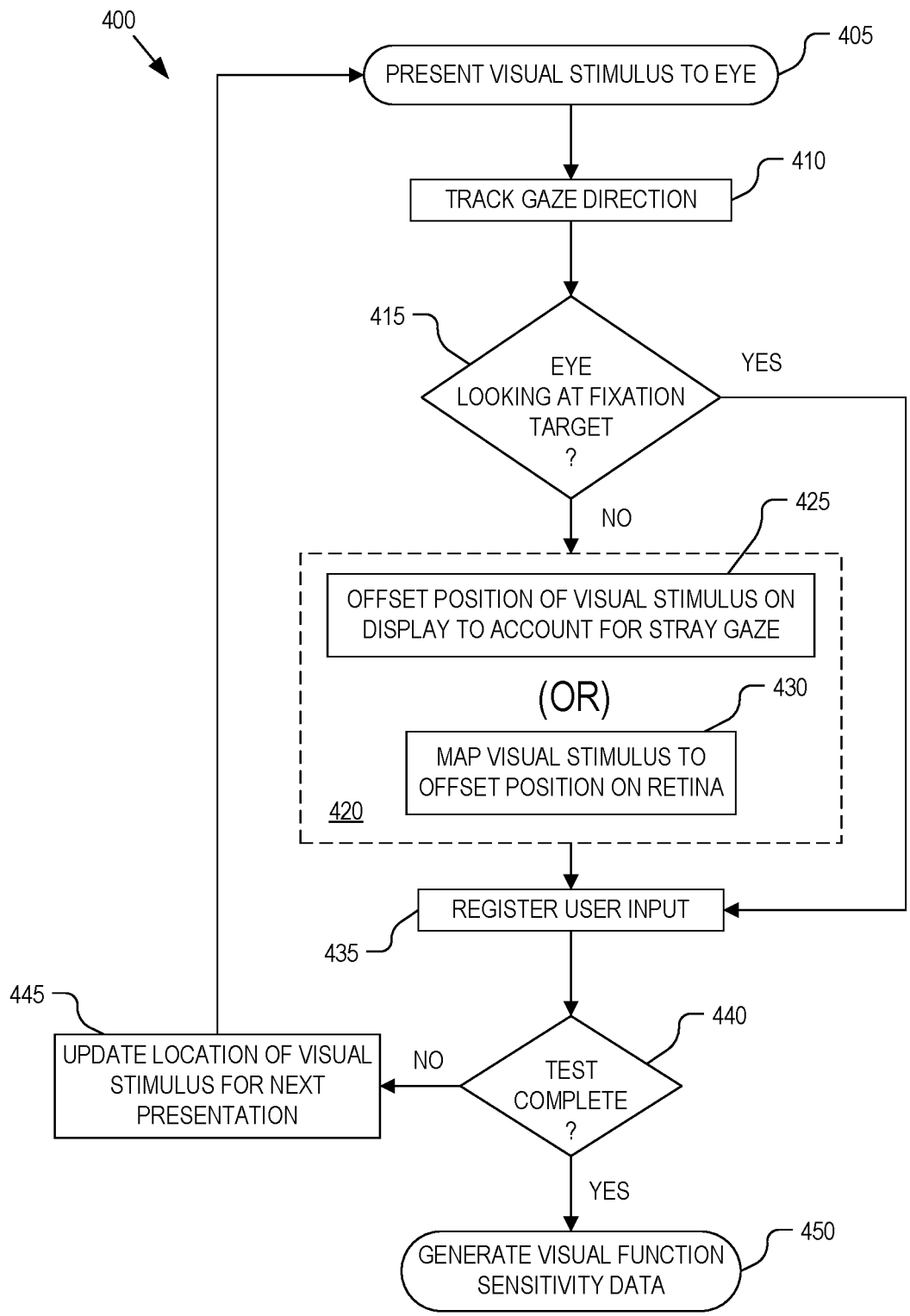
FIG. 4 is a flow chart illustrating a process of operating the ophthalmic testing system while performing a visual field test, in accordance with an embodiment of the disclosure.

FIG. 4 is a flow chart illustrating a process 400 of operation of ophthalmic testing system 300 while performing a visual field test, in accordance with an embodiment of the disclosure. Process 400 is described with reference to FIGS. 5A and 5B. The order in which some or all of the process blocks appear in process 400 should not be deemed limiting. Rather, one of ordinary skill in the art having the benefit of the present disclosure will understand that some of the process blocks may be executed in a variety of orders not illustrated, or even in parallel.

With fixation target 105 presented in the center of display 110, in a process block 405, controller 305 operates display 110 to present a first visual stimulus 115A to eye 120. Visual stimulus 115A may assume a variety of different shapes, colors, and patterns; however, in one embodiment, visual stimulus 115A is a monochromatic dot (e.g., red dot, black dot, etc.). Contemporaneously with presenting visual stimulus 115A (and in some embodiments includes prior to presenting visual stimulus 115A), controller 305 uses retinal camera 310 to track gaze direction 125 of eye 120. Retinal camera 310 is focused on retina 121 of eye 120 and uses anatomical features of retina 121 for monitoring gaze direction 125 in real-time. In one embodiment, retinal camera 310 includes an integrated image signal processor that internally analyzes retinal images and outputs gaze tracking data in real-time to controller 305. Controller 305 then uses the gaze tracking data, as opposed to the retinal images themselves, to determine whether eye 120 is fixated on fixation target 105.

If gaze direction 125 of eye 120 is determined to be aligned with fixation target 105 within an acceptable threshold (decision block 415; see FIG. 5A), then process 400 continues to process block 435 where the user's input indicating whether they saw or didn't see visual stimulus 115A is registered. However, if controller 305 determines that gaze direction 125 of eye 120 has drifted away from fixation target 105 during presentation of visual stimulus 115A (decision block 415; see FIG. 5B), then process 400 continues to general process block 420 to offset an intended position associated with visual stimulus 115A and compensate for the drifting of gaze direction 125 from fixation target 105 during presentation of visual stimulus 115A.

General process block 420 can be implemented by either one of process block 425 or process block 430. In process block 425, the intended position associated with visual stimulus 115A is an intended display position 515A. When gaze direction 125 is fixated on fixation target 105 (see FIG. 5A), display position 515B (which is physically the same as intended display position 515A in FIG. 5B) stimulates retinal position 520A and operates as a visual function sensitivity test of retinal position 520A. However, since gaze direction 125 has drifted or strayed from fixation target 105 (see FIG. 5B), intended display position 515A no longer stimulates intended retinal position 520B (which is the same physical location on retina 121 as retinal position 520A). Rather, intended display position 515A ends up stimulating a different portion of retina 121, thereby spoiling the visual field test results, unless the gaze drifting is compensated. Accordingly, in process block 425, intended display position 515A is offset, or physically shifted on display 110, to offset display position 525 by an amount and a direction (i.e., vector offset) that causes visual stimulus 115A (as offset in FIG. 5B) to stimulate intended retinal position 520B on retina 121. Intended retinal position 520B is equivalent to retinal position 520A, which is stimulated by display position 515B (see FIG. 5A) when gaze direction 125 is aligned with fixation target 105. Accordingly, process block 425 offsets the position of visual stimulus 115A by a vector offset that compensates for the drifting of gaze direction 125.

Figure 5A:
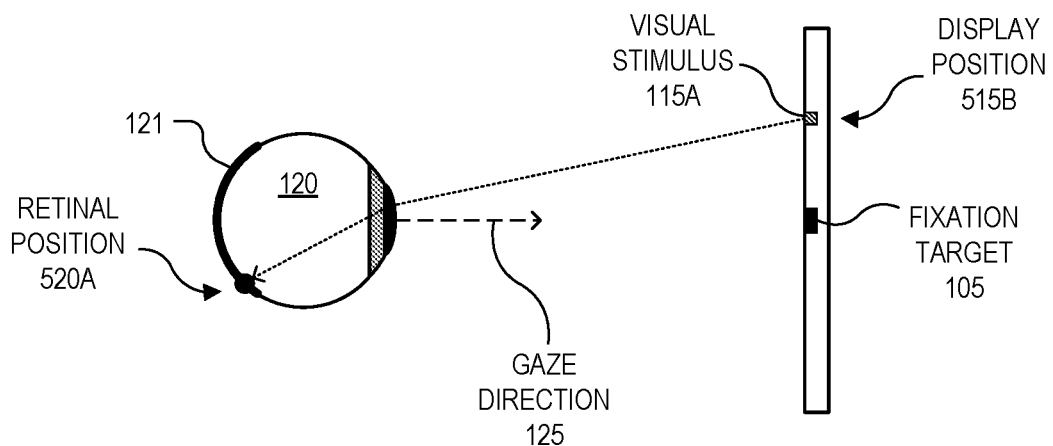
FIG. 5A illustrates an eye having a gaze direction that remains fixated on a fixation target while a visual stimulus is presented on a display, in accordance with an embodiment of the disclosure.
Figure 5B:
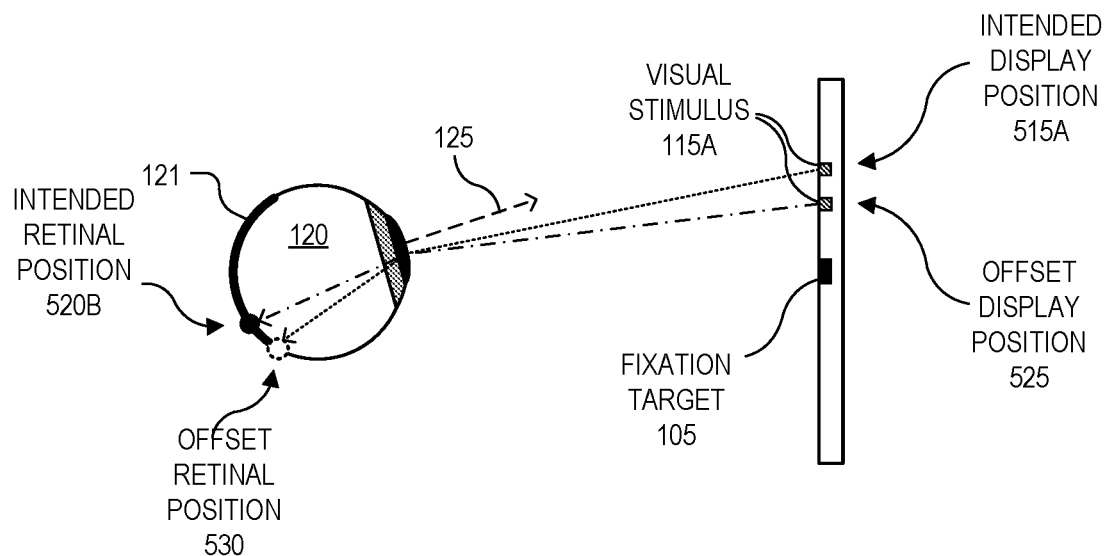
FIG. 5B illustrates an eye having a gaze direction that has drifted from the fixation target while a visual stimulus is presented on a display, in accordance with an embodiment of the disclosure.

Optionally, process block 430 may be executed to offset an intended position associated with visual stimulus 115A to compensate for drifting of gaze direction 125 from fixation target 105 during presentation of visual stimulus 115A. In process block 430, the intended position associated with visual stimulus 115A is intended retinal position 520B on retina 121, which would be stimulated if gaze direction 125 was aligned with fixation target 105, as illustrated in FIG. 5A. Accordingly, instead of offsetting the physical position of visual stimulus 115A on display 110, intended retinal position 520B is mapped to offset retinal position 530 that is actually stimulated by visual stimulus 115A in its intended display position 515A. Accordingly, general process block 420 offsets an intended position associated with visual stimulus 115A to compensate for drifting of gaze direction 125 by either shifting the physical position of visual stimulus 115A on display 110 in real-time based upon gaze tracking data from retinal camera 310, or remaps the intended retinal position 520B being tested to an offset retinal position 530 based upon the gaze tracking data from retinal camera 310.

In some cases the user's gaze direction 125 may drift or scan in multiple different directions during the presentation of a single visual stimulus 115A. Accordingly, in some embodiments, the mapping of a given visual stimulus is time weighted across multiple offset intended positions on retina 121, when gaze direction 125 is determined to have moved during presentation of a given visual stimulus. Accordingly, the user's input associated with a given visual stimulus 115 may be time weighted and mapped to multiple offset intended positions (e.g., multiple offset retinal positions).

With the intended position associated with visual stimulus 115A is offset to compensate for drifting of gaze direction 125, the user input indicating whether the user acknowledges observance of visual stimulus 115A is registered (process block 435). In this manner the visual field testing technique of process 400 does not reject user inputs acquired when the user's gaze direction 125 has drifted off of fixation target 105, but rather offsets and compensates for this gaze drifting.

The visual field testing of process 400 continues to loop by updating the location of the next visual stimulus 115B, C . . . (process block 445) to test the visual function sensitivity of eye 120 over the user's FOV by testing a variety of different locations throughout retina 121. Once retina 121 has been adequately tested over the user's FOV, the visual field test is completed (decision block 440) and a visual function sensitivity map (e.g., numerical map 205, heat map 210, etc.) is generated for doctor/patient review. The visual function sensitivity maps generated by process 400 are generated using user inputs that include inputs registered both while gaze direction 125 was fixated on fixation target 105 (e.g., FIG. 5A) and while gaze direction 125 drifted from fixation target 105 (e.g., FIG. 5B). Since inputs acquired while gaze direction 125 has drifted are used, the visual field test of process 400 reduces the testing time compared to conventional visual field tests.

Figure 6:
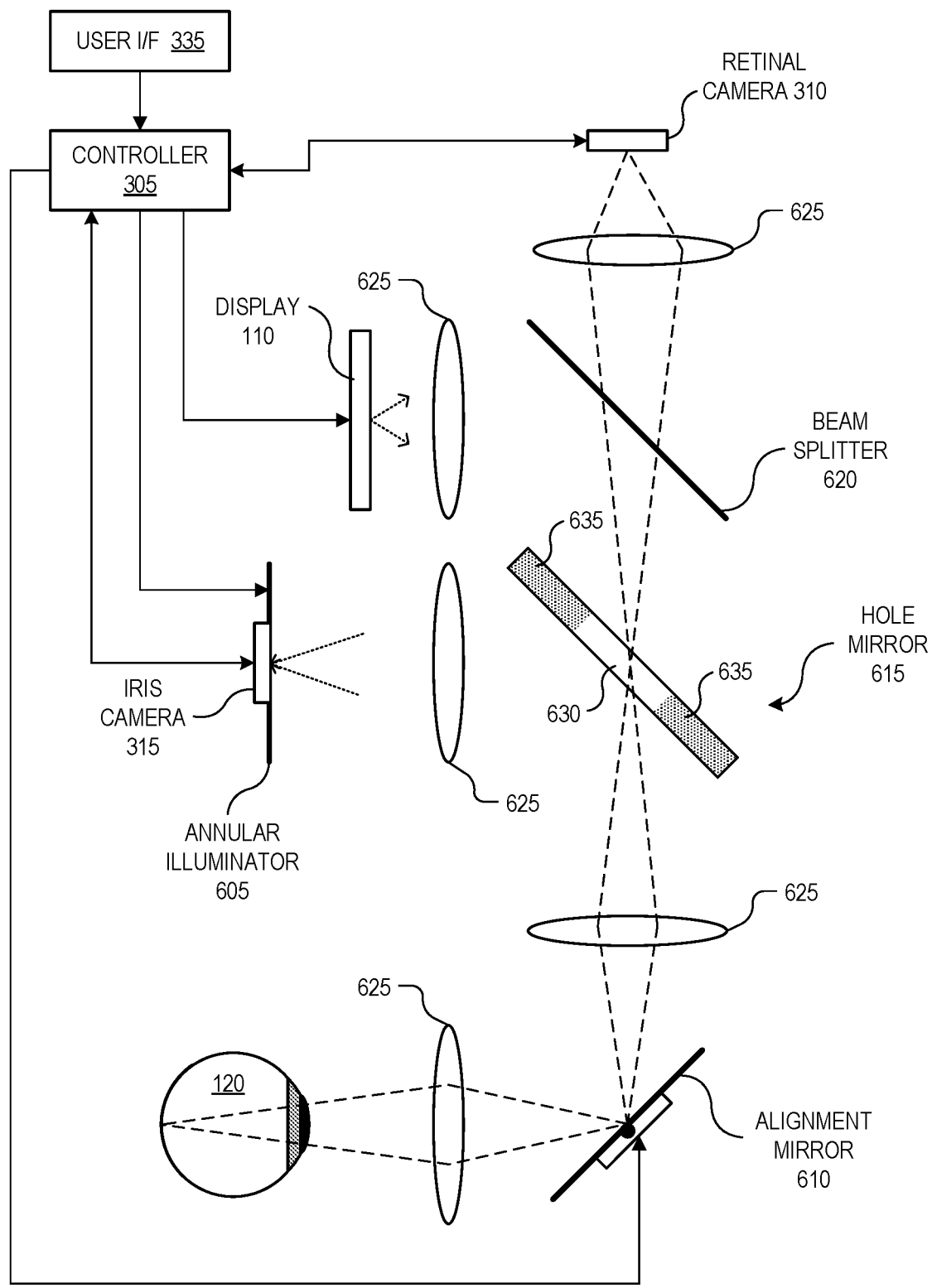
FIG. 6 is an example optical implementation of the ophthalmic testing system described in FIG. 3, in accordance with an embodiment of the disclosure.

FIG. 6 is an example ophthalmic testing system 600, in accordance with an embodiment of the disclosure. System 600 is one possible optical implementation of ophthalmic testing system 300 described and illustrated in FIG. 3. The illustrated embodiment of system 600 includes controller 305, retinal camera 310, iris camera 315, display 110, an annular illuminator 605, memory 340 (not illustrated in FIG. 6), alignment mirror 610, hole mirror 615, beam splitter 620, and lenses 625. The illustrated embodiment of hole mirror 615 includes a central section 630 and a peripheral section 635. Annular illuminator 605 incorporates the functionality provided by both IR illuminator 325 and flash illuminator 330. System 600 operates in the same manner as system 300 as described in connection with FIGS. 3 and 4 to perform a visual field test.

Central section 630 of hole mirror 615 is substantially transmissive to visible light and aligned to pass retinal images of retina 121 within eye 120 to retinal camera 310. In contrast, peripheral section 635 is substantially reflective to IR light and reflects IR iris images from eye 120 to iris camera 315 and reflects IR light from annular shaped illuminator 605 to eye 120. In one embodiment, peripheral section 635 is substantially reflective to both IR light and visible light to reflect white light flashed from annular illuminator 605 into eye 120 for acquiring retinal images of retina 121. The retinal images are then passed through central section 630 to retinal camera 310. In one embodiment, central section 630 is coated with one or more optical films (e.g., dichroic coatings) to substantially pass light with wavelengths below 900 nm while substantially reflecting light above 900 nm. Hole mirror 615 serves to reduce ghost images from annular illuminator 605 from reaching retinal camera 310. In one embodiment, iris camera 315 is disposed in a center of annular illuminator 605, which has an annular shape. As discussed above, iris camera 315 operates to track gross movements of eye 120, such as blinking and gross gaze tracking, by tracking or imaging the iris and/or pupil of eye 120.

Beam splitter 620 is positioned to pass a portion of the light of retinal images to retinal camera 310 while reflecting display light including fixation target 105 and visual stimuli 115 to eye 120. In some embodiments, beam splitter 620 is more transmissive than reflective. In one embodiment, beam splitter 620 is approximately 90% transmissive and 10% reflective. Other reflectance/transmittance ratios may be implemented. Alignment mirror 610 is provided to align eye 120 into the optical system. In the illustrated embodiment, alignment mirror 610 is coupled to controller 305 to provide auto-alignment. In other embodiments, alignment mirror 610 may be manually adjusted (e.g., pivoted) as an initial setup. Lenses 625 are provided throughout system 600 to provide image and light focusing in the optical paths.

Figure 7:
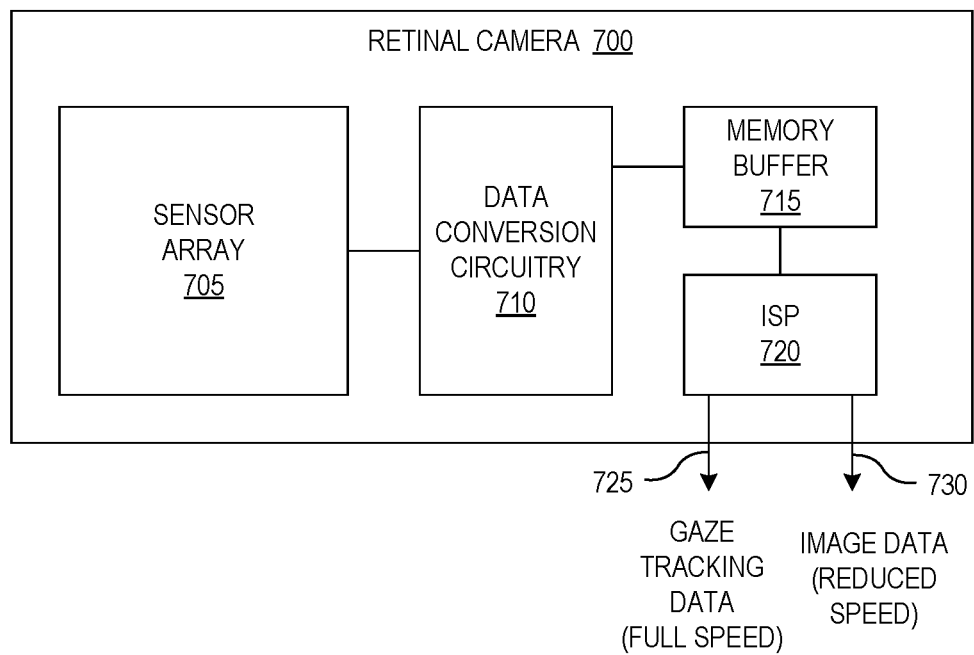
FIG. 7 is a functional block diagram of a retinal camera including an integrated image signal processor, in accordance with an embodiment of the disclosure.

FIG. 7 is a functional block diagram of a retinal camera 700 including an integrated image signal processor, in accordance with an embodiment of the disclosure. Retinal camera 700 is one possible implementation of retinal camera 310. The illustrated embodiment of retinal camera 700 includes a two-dimensional sensor array 705, data conversion circuitry 710, a memory buffer 715, an integrated image signal processor (ISP) 720, a higher speed output port 725 and a slower speed output port 730.

During operation, two-dimensional image data (e.g., retinal images) is acquired by sensor array 705 and converted from the analog domain to the digital domain by data conversion circuitry 710. The image data is acquired at a full frame rate (e.g., 30 frames per second) and stored into memory buffer 715. ISP 702 operates on the buffered retinal image frames to generate gaze tracking data and composite or mosaic retinal image data. The gaze tracking data is generated in real-time and output on higher speed output port 725 to controller 305. In one embodiment, the gaze tracking data is output on higher speed output port 725 at the full frame rate (e.g., 30 frames per second). In one embodiment, the gaze tracking data is output at a substantially high rate than the inverse of the duration of a given visual stimulus. For example, in one embodiment, gaze tracking data is refreshed and output on higher speed output port 725 at or above 100 Hz. In contrast, the retinal images or mosaic retinal images are output at a reduced speed on slower speed output port 730.

Using higher speed output port 725 to output gaze tracking data while using slower speed output port 730 for image data enables controller 305 to perform real-time gaze tracking based upon retinal images, while giving retinal camera 700 more time to generate high quality composite or mosaic retinal images.

Figure 8:
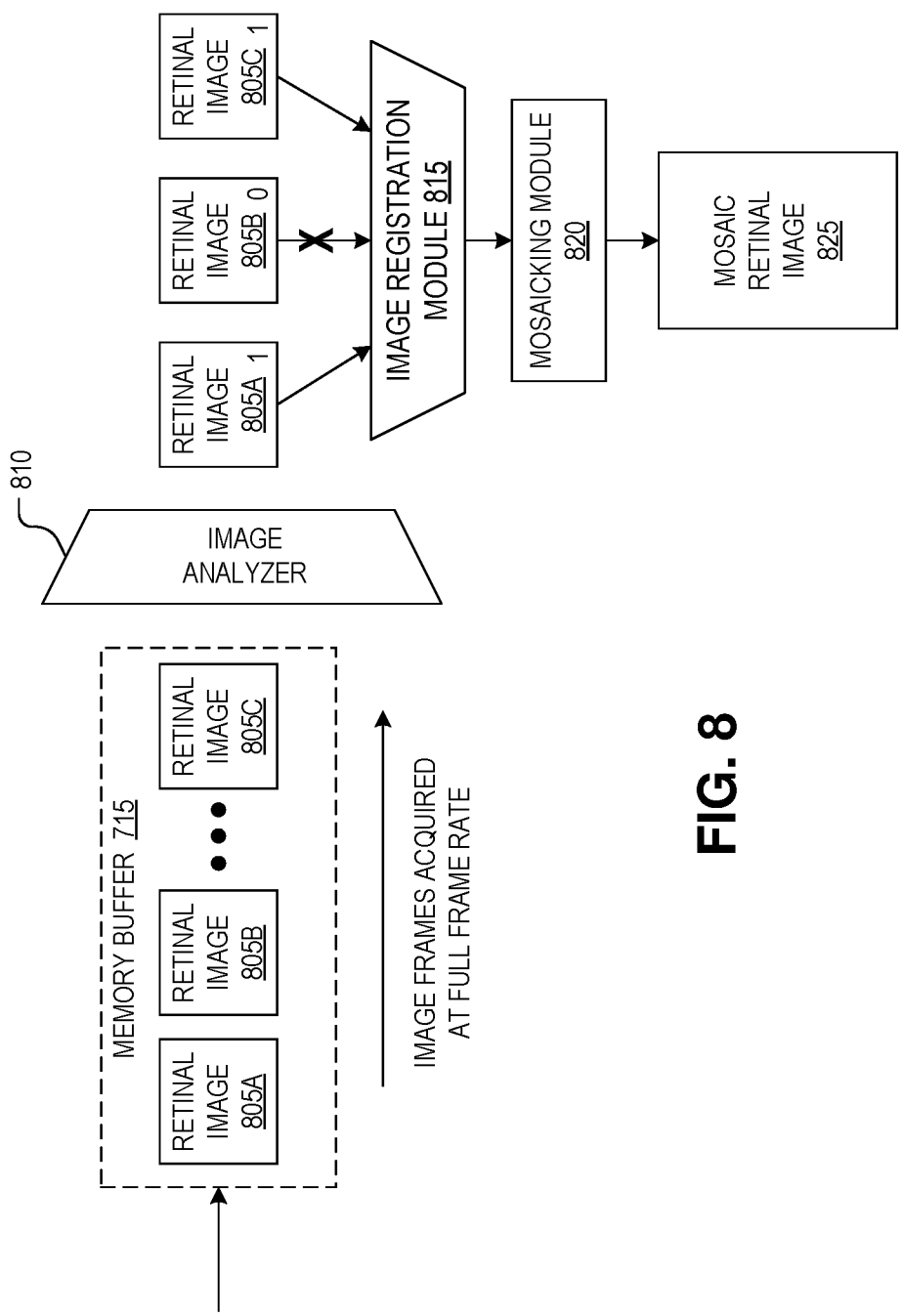
FIG. 8 is a block flow diagram illustrating image processing by a retinal camera including an integrated image signal processor, in accordance with an embodiment of the disclosure.

FIG. 8 is a block flow diagram illustrating image processing by retinal camera 700 that leverages the benefits of having the integrated ISP 720 to acquire high quality mosaic retinal images, in accordance with an embodiment of the disclosure. As illustrated, retinal images 805A-C are acquired by sensor array 705 at a full frame rate (e.g., 30 frames per second), converted into the digital domain by data conversion circuitry 710, and buffered into memory buffer 715. An image analyzer 810 is executed by ISP 720 to analyze the buffered retinal images 805 (a sort of preprocessing) to determine which of retinal images 805 are of sufficient quality and which are of insufficient quality. For example, image analyzer 810 may analyze retinal images 805 for images that are unacceptably blurred, do not have sufficient contrast to be useful, are washed out, and/or include unacceptable corneal reflections. Images that are deemed unacceptable are flagged unacceptable (e.g., marked with a zero bit) while images that are deemed acceptable are flagged as such (e.g., marked with a one bit). The images flagged as unacceptable may be discarded. The images marked as acceptable are registered to each other (e.g., pixel-to-pixel alignment) by image registration module 815, and then combined by mosaicking module 820 into a single mosaic retinal image 825. Mosaicking module 820 may combine images to generate high dynamic range images, to generate larger images having a larger FOV of retina 121 based upon a series of smaller partially overlapping retinal images, or otherwise. For example, in one embodiment, each image acquired may be shifted by just one, two, three, or more pixels both vertically and/or horizontally. By aligning and combining smaller retinal images, each shifted by a few pixels and generated based upon a smaller spot size illuminated through the pupil, into larger mosaic images 825, the likelihood of deleterious corneal reflections due to misalignments are reduced while achieving a high dynamic range. Furthermore, any of retinal image frames 805 spoiled by misalignment are simply flagged, discarded, and not used to generate the larger mosaic retinal image 825. Since mosaic retinal images 825 are output on the slower speed output port 730, ISP 720 is given more time to perform the image processing while still outputting gaze tracking data at the higher speed on higher speed output port 725 to controller 305 for real-time tracking.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An apparatus for ophthalmic testing, comprising:
   a display for presenting visual stimuli to an eye;

a camera for tracking a gaze direction of the eye while the visual stimuli is presented to the eye;
a controller coupled to the display and the camera, the controller including a machine-readable storage medium storing instructions that, when executed by the controller, will cause the apparatus to perform operations, including:
sequentially presenting the visual stimuli on the display for measuring a visual function sensitivity of the eye over a field of view;
monitoring a gaze direction of the eye with the camera to identify when the gaze direction has drifted from a fixation target;
mapping a first intended retinal position on a retina, which is associated with a first visual stimulus of the visual stimuli, to an offset retinal position that is actually stimulated by the first visual stimulus due to a drifting of the gaze direction, wherein the mapping compensates for the drifting of the gaze direction from the fixation target when the gaze direction is determined to have drifted during presentation of the first visual stimulus, wherein the first intended retinal position is stimulated by the first visual stimulus on the display when the gaze direction is aligned with the fixation target; and
registering user inputs indicating whether the user acknowledges observance of each of the visual stimuli presented.

2. The apparatus of claim 1, wherein the machine-readable storage medium stores further instructions that, when executed by the controller, will cause the apparatus to perform further operations, comprising:
generating a visual function sensitivity map of the eye based upon the user inputs including the user inputs registered while the gaze direction drifted from the fixation target.

3. The apparatus of claim 1, wherein the camera comprises a retinal camera for capturing retinal images of a retina of the eye and wherein monitoring the gaze direction of the eye with the camera comprises tracking anatomical features of the retina in real-time with the retinal camera.

4. The apparatus of claim 3, further comprising:
an annular shaped illuminator coupled to the controller for illuminating the retina with infrared light while monitoring the gaze direction of the eye.

5. The apparatus of claim 4, further comprising:
an iris camera coupled to the controller and disposed in a center of the annular shaped illuminator, the iris camera configured to track gross movements of the eye by tracking at least one of an iris or a pupil of the eye; and
a hole mirror having a central section and a peripheral section surrounding the central section, wherein the central section is substantially transmissive to visible light and aligned to pass the retinal images from the eye to the retinal camera and the peripheral section is substantially reflective to reflect infrared iris images from the eye to the iris camera and to reflect the infrared light from the annular shaped illuminator to the eye.

6. The apparatus of claim 3, wherein the retinal camera includes an integrated image signal processor that generates gaze tracking data based upon the retinal images, wherein the integrated signal processor is coupled to the controller to output the gaze tracking data to the controller, and wherein monitoring of the gaze direction is executed by the controller based upon the gaze tracking data output from the retinal camera.

7. The apparatus of claim 6, wherein the retinal camera includes a higher-speed output port coupled to output the gaze tracking data to the controller and a slower-speed output port coupled to output the retinal images to the controller.

8. A method for performing a visual field test on an eye, the method comprising:
sequentially presenting visual stimuli to the eye on a display;
monitoring a gaze direction of the eye with a camera to identify when the gaze direction has drifted from a fixation target;
offsetting a first intended position associated with a first visual stimulus of the visual stimuli to compensate for drifting of the gaze direction from the fixation target when the gaze direction is determined to have drifted during presentation of the first visual stimulus;
registering user inputs indicating whether the user acknowledges observance of each of the visual stimuli presented; and
time weighting a given one of the user inputs across multiple offset intended positions when the gaze direction is determined to have moved during presentation of the given one of the visual stimuli.

9. The method of claim 8, further comprising:
generating a visual function sensitivity map of the eye based upon the user inputs including the user inputs registered while the gaze direction drifted from the fixation target.

10. The method of claim 8, wherein the first intended position comprises a first intended retinal position on a retina of the eye that is stimulated by the first visual stimulus on the display when the gaze direction is aligned with the fixation target.

11. The method of claim 10, wherein offsetting the first intended position associated with the first visual stimulus to compensate for drifting of the gaze direction comprises:
mapping the first intended retinal position associated with the first visual stimulus to an offset retinal position that is stimulated by the first visual stimulus due to the drifting of the gaze direction.

12. The method of claim 8, wherein the first intended position comprises a first intended display position on the display.

13. The method of claim 12, wherein offsetting the first intended position associated with the first visual stimulus to compensate for drifting of the gaze direction comprises:
offsetting the first intended display position at which the first visual stimulus is presented on the display by an amount and a direction that causes the first visual stimulus to stimulate a first intended retinal position on a retina of the eye associated with the first intended display position on the display when the gaze direction is aligned with the fixation target.

14. The method of claim 8, wherein the camera comprises a retinal camera for capturing retinal images of a retina of the eye and wherein monitoring the gaze direction of the eye with the camera comprises tracking anatomical features of the retina in real-time with the retinal camera.

15. The method of claim 14, wherein the retinal camera includes an integrated image signal processor that generates gaze tracking data based upon the retinal images, and wherein monitoring of the gaze direction is executed based upon the gaze tracking data output from the integrated image signal processor of the retinal camera.

16. The method of claim 15, further comprising:
acquiring the retinal images at a full frame rate;

outputting the gaze tracking data from the retinal camera on a first port at the full frame rate;

analyzing multiple ones of the retinal images within the integrated image signal processor to determine which of the retinal images are of sufficient quality and which are of insufficient quality;

discarding the retinal images determined to be of insufficient quality;

generating a mosaic retinal image based upon the retinal images determined to be of sufficient quality; and outputting the mosaic retinal images from the retinal camera on a second port at a reduced frame rate which is less than the full frame rate.

17. The method of claim 16, wherein the retinal images comprise a plurality of shifted retinal images and wherein generating the mosaic retinal image comprises aligning the shifted retinal images when combining the shifted retinal images into the mosaic retinal image.

18. The method of claim 15, wherein the gaze tracking data is updated at a higher refresh rate than an inverse of a duration that each of the visual stimuli are presented to the eye on the display.

\* \* \* \* \*